US005593414A

United States Patent [19]
Shipp et al.

[11] Patent Number: 5,593,414
[45] Date of Patent: Jan. 14, 1997

[54] METHOD OF APPLYING A SURGICAL LIGATION CLIP

[75] Inventors: John I. Shipp, Tullahoma, Tenn.; George Crothall, Santa Clara, Calif.; Robert L. Lathrop, Jr., San Jose, Calif.; Donald R. Reichel, Saratoga, Calif.

[73] Assignee: Apollo Camera, L.L.C., Tullahoma, Tenn.

[21] Appl. No.: 407,038

[22] Filed: Mar. 17, 1995

Related U.S. Application Data

[63] Continuation of Ser. No. 111,634, Aug. 25, 1993, abandoned.

[51] Int. Cl.⁶ .................................................. A61B 17/122
[52] U.S. Cl. .................................................. 606/142; 606/158
[58] Field of Search ......................................... 606/157, 158, 606/142, 120

[56] References Cited

U.S. PATENT DOCUMENTS

| | | | |
|---|---|---|---|
| 3,056,408 | 10/1962 | Brown | 606/142 X |
| 3,476,114 | 11/1969 | Shannon et al. | 606/139 |
| 4,024,868 | 5/1977 | Williams | 606/158 |
| 4,274,415 | 6/1981 | Kanamoto et al. | 606/158 X |
| 4,340,061 | 7/1982 | Kees et al. | 606/158 |
| 4,487,205 | 12/1984 | Di Giovanni et al. | 606/142 X |
| 4,556,060 | 12/1985 | Perlin | 606/158 |
| 4,658,822 | 4/1987 | Kees | 606/158 |
| 4,777,949 | 10/1988 | Perlin | 606/158 |
| 4,777,950 | 10/1988 | Kees | 606/158 |
| 4,943,298 | 7/1990 | Fujita et al. | 606/158 |
| 4,961,743 | 10/1990 | Kees et al. | 606/158 |
| 4,966,603 | 10/1990 | Focelle et al. | 606/158 |
| 5,342,373 | 8/1994 | Stefanchik et al. | 606/142 |
| 5,368,600 | 11/1994 | Failla et al. | 606/139 |

FOREIGN PATENT DOCUMENTS

| | | | |
|---|---|---|---|
| 1389762 | 4/1988 | U.S.S.R. | 606/158 |

*Primary Examiner*—Michael H. Thaler
*Attorney, Agent, or Firm*—Waddey & Patterson; I. C. Waddey, Jr.

[57] ABSTRACT

A surgical ligation clip is preformed from a continuous piece of metal wire to assume a shape having a reduced cross-sectional area. A clamping arm of the clip is alternately moveable from a clamped to an unclamped position above a vessel support member. A tension coil joins the vessel support member to the clamping arm and provides the hemostatic clamping force from the clip to the targeted blood vessel.

4 Claims, 10 Drawing Sheets

METHOD OF APPLYING A SURGICAL LIGATION CLIP

This application is a continuation of U.S. patent application Ser. No. 08/111,634 filled Aug. 25, 1993, now abandoned.

BACKGROUND OF THE INVENTION

The present invention relates generally to mechanical devices used in surgical procedures to obtain ligation or hemostasis, and more particularly, to a ligation clip used during surgery to clamp around a vessel or duct, such as the cystic duct, and thereby obtain ligation.

It will be appreciated by those skilled in the art that the use of ligation clips to control bleeding during surgical procedures is well known. As described, for example, in U.S. Pat. Nos. 4,976,722 and 4,979,950, prior art clips are generally formed of metal wire, usually a titanium alloy, having a "U-shaped" rectangular cross-section. Such prior art clips often include a grooved pattern machined into the inner or clamping surfaces of the clip, in an attempt to enhance the ability of the clip to remain in position after it is closed around the vessel. Application of the clip to the vessel is normally effected by means of a crushing action produced by a clip applier, such as that disclosed in U.S. Pat. No. 5,030,226. Such crushing actions, of course, permanently deform the clips, making them difficult to remove or reposition.

Prior art surgical ligation clips have several inherent problems. For example, the force applied by the clip to the vessel can be variable and inconsistent from one clip to the next, because of the variation in crushing force applied to the clip by the user. Further, prior art clips have a tendency to slip off the end of the blood vessel stub to which it has been applied, because of the low coefficient of friction associated with the clip, and lack of adequate restraining force provide by the clip. Because of this, separation of the clip from the vessel to which it has been applied, after the wound has been closed, is not uncommon.

It is also common in the prior art to actually form and crush the clip only at the time of its application to the targeted blood vessel. Accordingly, the clip applier mechanism must be relatively large and cumbersome. This is a particular problem in laparoscopic procedures, during which both the clip and clip applier must be inserted through a trocar placed through the patient's external tissues and into the surgical field. Thus, prior art ligation clips used in laparoscopic procedures universally consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm diameter trocar port is highly desirable.

What is needed, then, is a surgical ligation clip that can be easily pre-formed into a shape that presents a minimal cross-sectional area, that can be easily applied to a vessel and that, when applied, will impart a consistent hemostatic force to the vessel while resisting separation from the vessel stub. This device is presently lacking in the prior art.

SUMMARY OF THE INVENTION

In order to achieve the objects of simplicity of manufacture, ease of use, consistency of clamping force, high resistance to lateral slippage, and presentation of minimal cross-sectional area during placement of the clip into the surgical field, a new and improved surgical clip was designed having a vessel clamping arm, a vessel support member, and a tension coil integrally joining the arm and support member. The clip is pre-formed so that in its relaxed state, it can be easily placed within the surgical field, including through a endoscopic trocar port with as little as a five millimeter diameter. After the clip is placed proximate the blood vessel or duct to be clamped, the clamping arm is moved from its relaxed position to a position under tension, allowing positioning of the vessel between the arm and support member. When correct placement and positioning is achieved, the arm is released and, as the arm tends to move back towards its relaxed position, it clamps the vessel between the arm's curved lower surface and the supporting upper surface of the vessel support member.

To enhance the performance of the tension coil, in a preferred embodiment of the invention, the vessel support member includes first and second arms, one of which terminates in a loop section. Minimal cross-sectional area of the clip is achieved by substantially longitudinally aligning the vessel support member, the clamping arm, the loop section, and the tension coil.

In a first embodiment of the clip, the clamping arm is pre-formed into a relaxed position whereby it extends slightly below the horizontal plan of the support member. A second embodiment of the clip preloads the clamping arm into a relaxed position where the free end of the arm rests against the upper surface of the support member.

DESCRIPTION OF THE PREFERRED EMBODIMENTS

Figure 1:
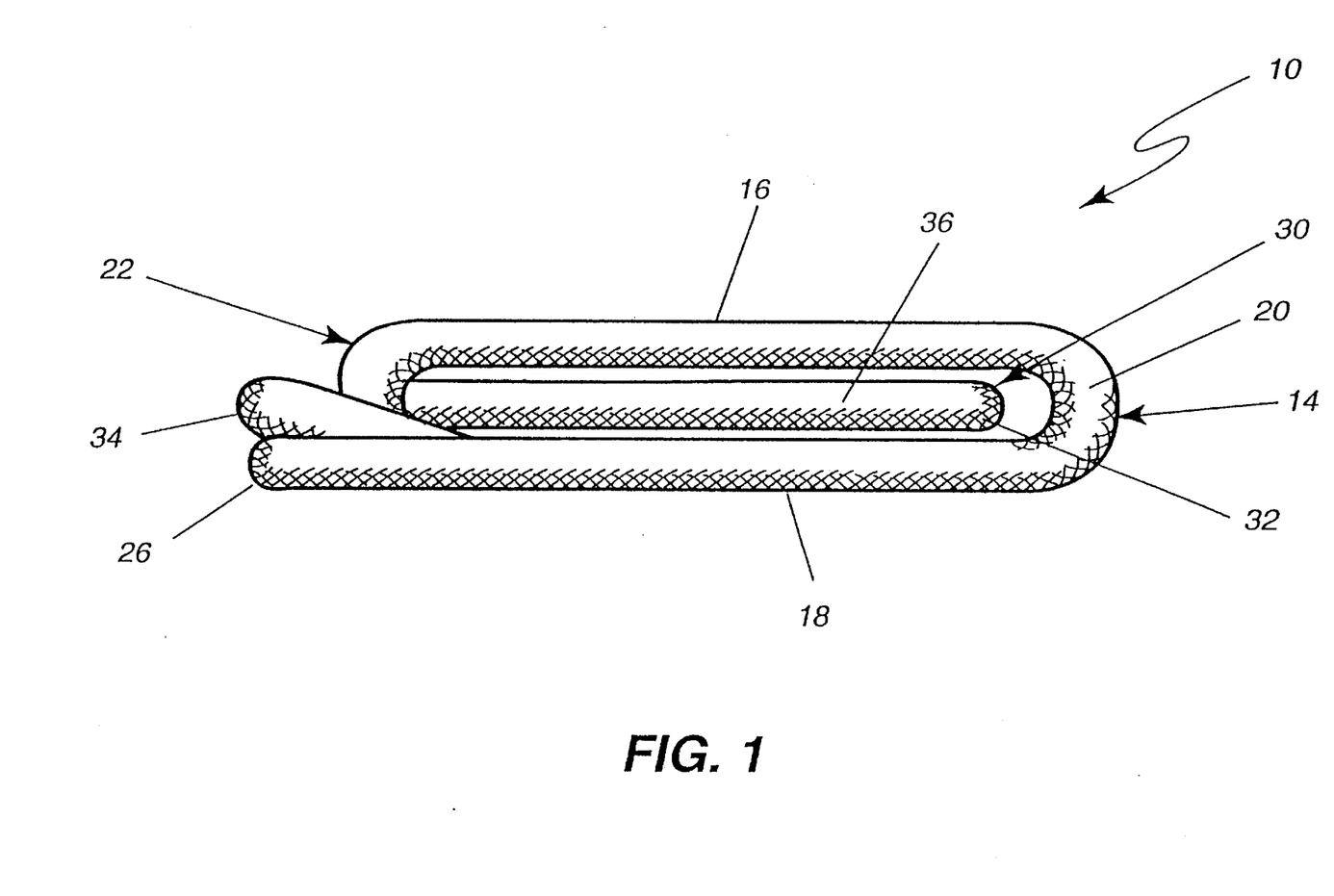
FIG. 1 is a top view of the surgical clip of the present invention with the vessel clamping member in a relaxed position.
Figure 2:
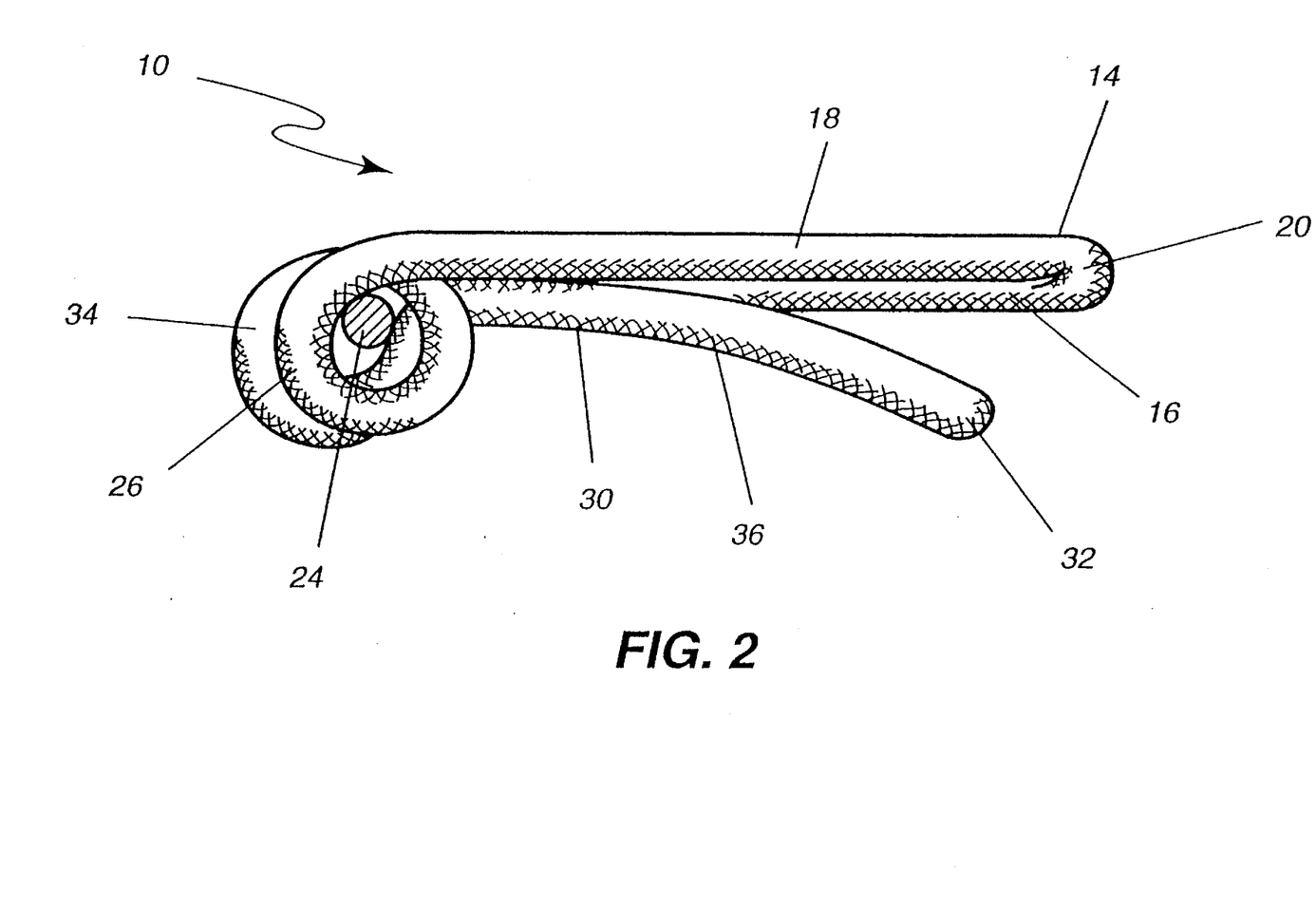
FIG. 2 is a side view of the surgical clip of the present invention with the vessel clamping member in a relaxed position.

Looking first at FIGS. 1 and 2, the surgical ligation clip of the present invention is shown in its relaxed position, prior to its manipulation into a position around the target blood vessel. Surgical clip 10 comprises generally a blood vessel clamping arm 30 which is moveable in a plane perpendicular to blood vessel support member 14. As seen best in FIG. 1, support member 14 is formed of a continuous piece of surgical wire, such as titanium or stainless steel, which is bent to define a first arm 16 and a substantially parallel second arm 18 joined by a one hundred eighty degree (180°) bend section 20. In the preferred embodiment, the proximal free end 24 of clip 10 will be joined to first arm 16 of support member 14 by a ninety degree (90°) bend section 22.

Second arm 18 terminates at its proximal end (away from one hundred eighty (180°) bend section 20) in loop section 26, the plane of which is perpendicular to the plane of support member 14 and which loops inwardly toward clamping arm 30.

In its relaxed position as shown in FIGS. 1 and 2, clamping arm 30 is longitudinally aligned with and oriented between first arm 16 and second arm 18 of support member 14, but below the horizontal plane defined by first and second arms 16 and 18. The distal free end 32 of clip 10 defines the beginning of clamping arm 30. A curved section 36 of clamping arm 30 moves proximately away from free end 32, terminating in tension coil 34. The vertical plane established by tension coil 34 is oriented in substantial alignment with the vertical plane of loop section 26, and, accordingly, perpendicular to the horizontal plane of support member 14. It will be apparent to those skilled in the art that in this orientation, and by forming clip 10 of a continuous piece of resilient material, movement of clamping arm 30 will place clamping arm 30 under tension with respect to vessel support member 14. Further, such an orientation will minimize the width and cross-sectional area of clip 10 which is preferred, particularly in laparoscopic surgery.

Figure 3:
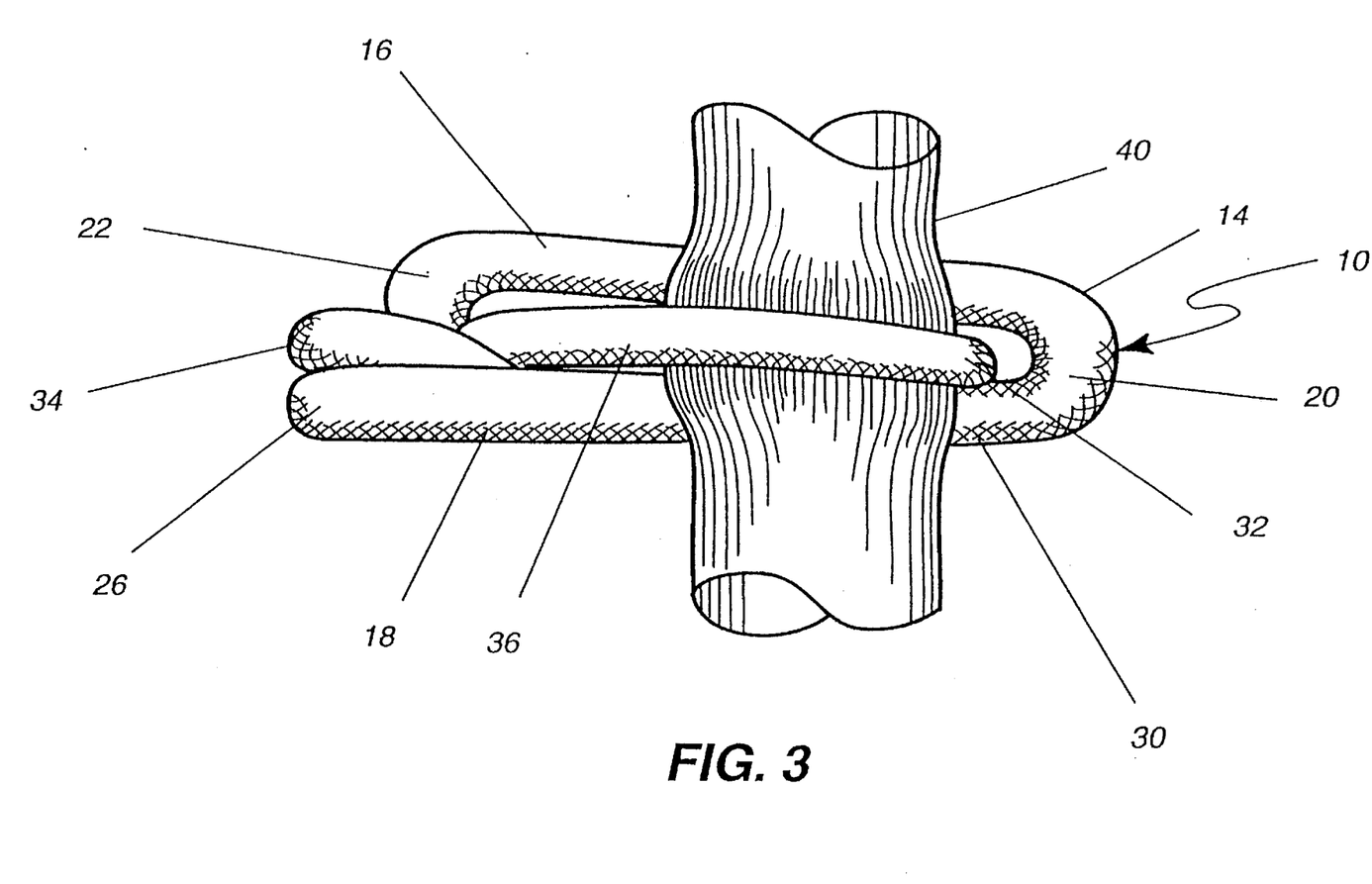
FIG. 3 is a top view of the surgical clip of the present invention after application to a blood vessel and with the vessel clamping arm in a clamped position.
Figure 4:
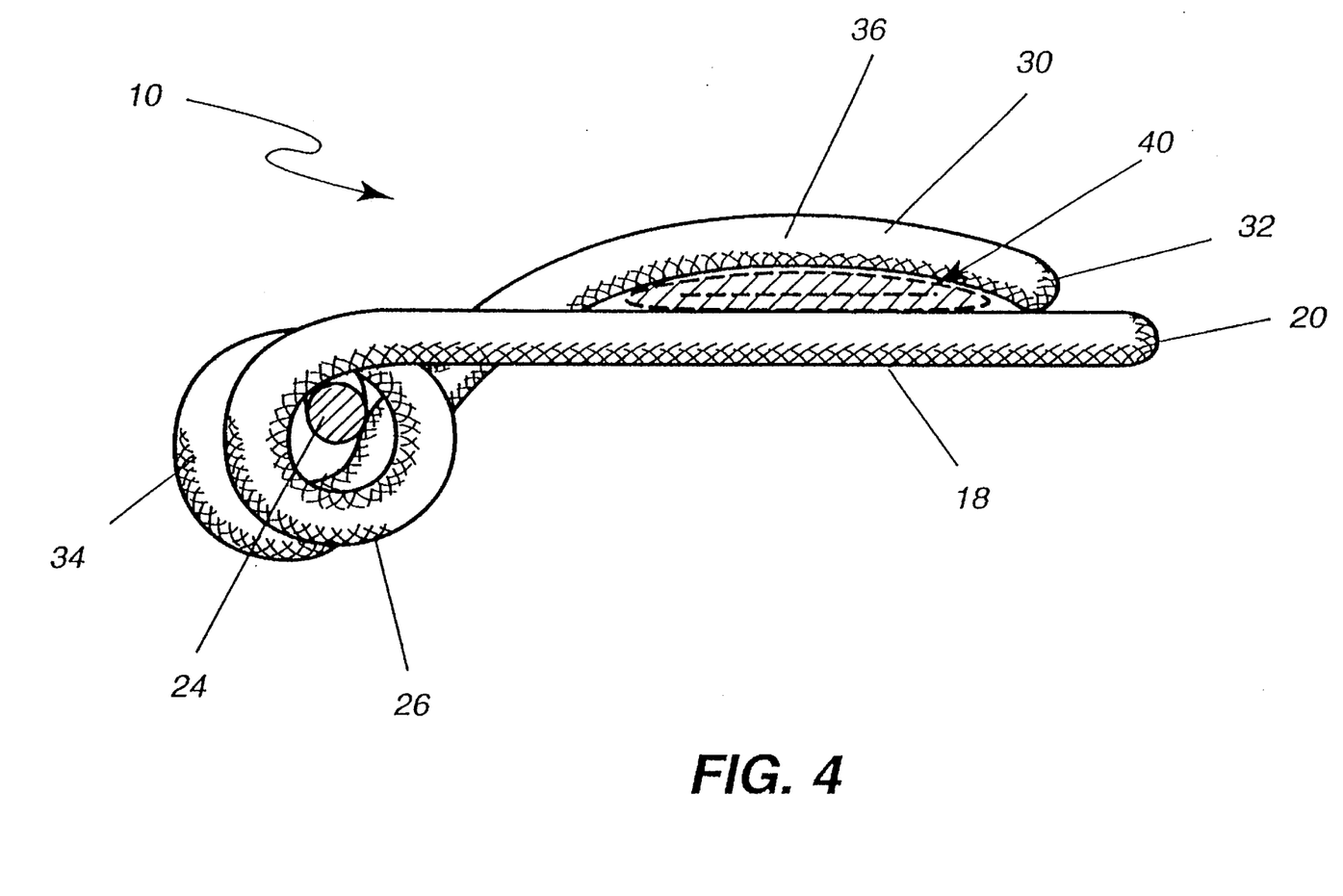
FIG. 4 is a side view of the surgical clip of the present invention after application to a blood vessel, showing the vessel clamping arm in a clamped position.

Looking now at FIGS. 3 and 4, application of clip 10 to a blood vessel 40 to achieve hemostasis is shown. After clip 10 is placed in the surgical field adjacent to the targeted blood vessel 40, clamping arm 30 is moved upwardly between vessel support member arms 16 and 18 to define a gap and space between distal free end 32 and the upper surface of one hundred eighty (180°) bend section 20. For most uses, a vertical gap of approximately 1.5 mm will be sufficient. Clip 10 is then maintained in this position so that blood vessel 40 can be manipulated within the space created between arm 30 and support member 14. Clamping arm 30 is then released, trapping vessel 40 within clip 10 as arm 30 moves toward its relaxed position. The curvature of curved section 36 of clamping arm 30 causes a relatively consistent clamping pressure to be placed over the entire surface of vessel 40, thereby achieving effective hemostasis. By placing loop section 26 physically adjacent to, and operatively in series with tension coil 34, a smoother, more consistent application of hemostatic force is obtainable, while increasing the resistance of clip 10 to deformation.

It will be apparent to those skilled in the art that clip 10 is also effective in clamping off ducts connecting various organs, the cystic duct for example. Accordingly, where the term "vessel" is used herein, it is intended that such reference include all fluid carrying body structures within the surgical field where ligation or clamping is needed. Where the diameter of a duct or other structure to be clamped is substantially larger than 1.5 mm, a slightly modified method of applying clip 10 is preferred so that the elastic limit of the material used in the construction of clip 10 is not exceeded. In such modified technique, surgical pliers of conventional design are first positioned over the area to be clamped and the duct or other structure is then compressed to approximately a two wall thickness, or 1.5 mm. The clip 10 is applied to the compressed duct and the pliers are then removed, yet another method of applying the clip 10 to achieve hemostasis of a blood vessel during surgery includes the steps of placing the pre-formed surgical ligation clip 10 having clamping arm 30 and vessel support member 14 proximate said vessel; compressing said vessel to a reduced diameter prior to placing the clip 10 around said vessel; bending the clamping arm 30 away from the vessel support member 14, thereby placing the clamping arm under tension; placing the clip 10 around the vessel whereby the vessel is positioned between the arm 30 and the support member 14; and releasing the clamping arm 30 thereby placing the vessel under tension between the arm 30 and the support member 14. To minimize the risk of over-compression, the pliers (not shown) will preferably include a means for limiting closure of its jaws to a minimum spacing of approximately 1.5 mm. The use of this technique on large structures allows clip 10 to be formed with a minimized profile suitable for use in a 5 mm trocar, even if the diameter of the duct to be clamped, for example, exceeds 5 mm.

To remove or re-position clip 10, clamping arm 30 needs merely to be moved back up into its fully unclamped position, the vessel and clip manipulated as needed, and then clamping arm 30 is released towards its relaxed position.

To counteract the tendency of clip 10 to produce a torsional force to blood vessel 40, it is preferred that the proximal free end of 24 of clip 10 join a ninety degree (90°) bend section 22 interposed between arm 16 and proximal free end 24. As shown on FIG. 2, free end 24 and a segment of bend section 22 is centrally disposed within tension coil 34.

Adding a series of ridges, notches, burrs by machining, etching, or other treatment to the clamping surfaces of arm 30 and support member 14 can enhance the gripping force of clip 10.

To achieve the objective of minimizing the cross-sectional area of clip 10, thereby permitting it to be used in laparoscopic surgical procedures, clip 10 is pre-formed into the position substantially as shown on FIGS. 1 and 2. In this configuration, arms 16 and 18, clamping arm 30, tension coil 34, and loop section 26 are in substantially alignment longitudinally.

In a preferred embodiment of the clip of the present invention, adaptable for placement within an endoscopic surgical field through a 5 mm diameter trocar port, the inside diameters of tension coil 34 and loop section 26 are approximately 3 mm. The length of clip 10, measured from the proximal surface of tension coil 34 to the distal surface of one hundred eighty (180°) degree bend section 20 is approximately 12 mm. The width of vessel support member 14, measured at the outside surfaces of first arm 16 and second arm 18, is approximately 2.5 mm. Clamping arm 30 is approximately 9 mm from distal free end 32 to its intersection with tension coil 34. In the preferred embodiment, curved section 36 of clamping arm 30 will have a radius of curvature of approximately 25 mm. A suitable material from which clip 10 can be formed is wrought titanium 6A1-4V ELI alloy wire having a nominal diameter of 0.75 mm, and which meets ASTM Standard F136-92. Clip 10 can also be made of wire having a non-circular cross section, or formed from wire having a combination of circular and non-circular sections. For example, tension coil 34 and/or clamping arm 30 could be stronger if formed from rectangular-shaped wire.

Figure 5:
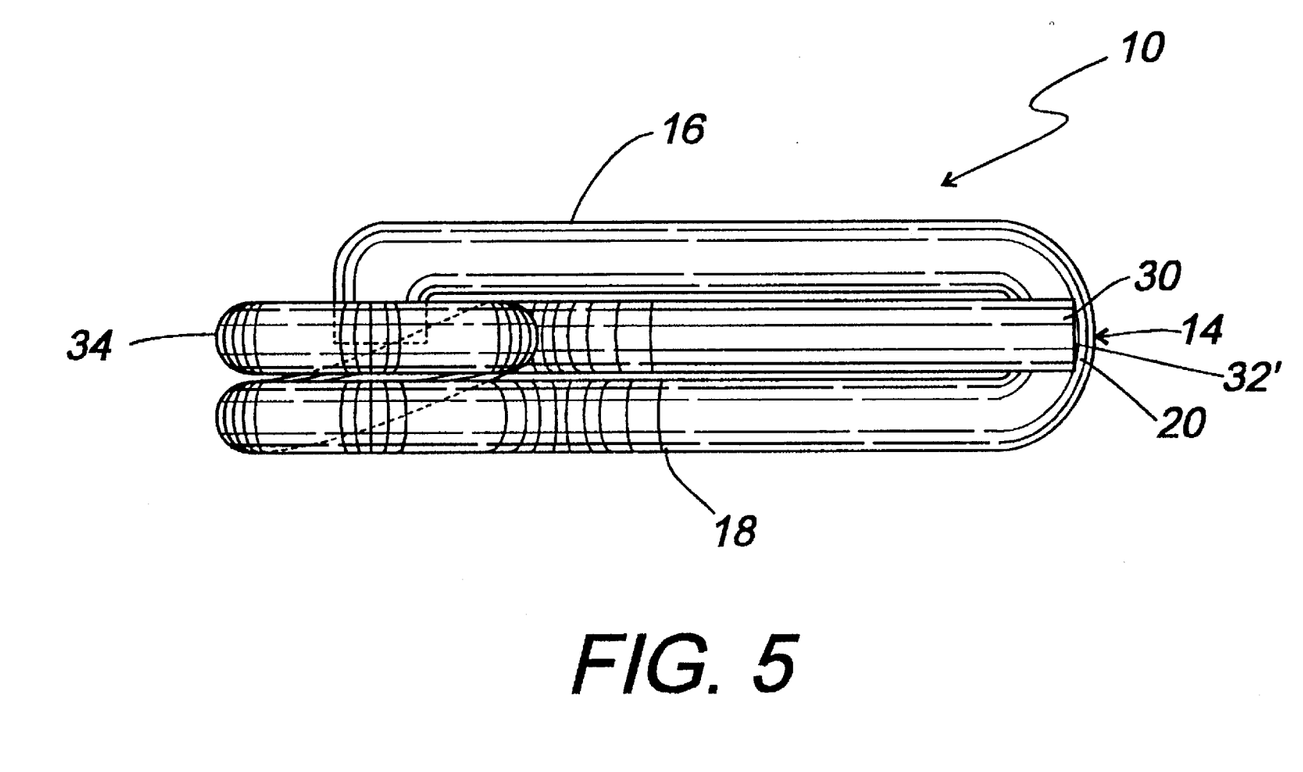
FIG. 5 is a top view of a second embodiment of the surgical clip of the present invention having a preloaded clamping arm.
Figure 6:
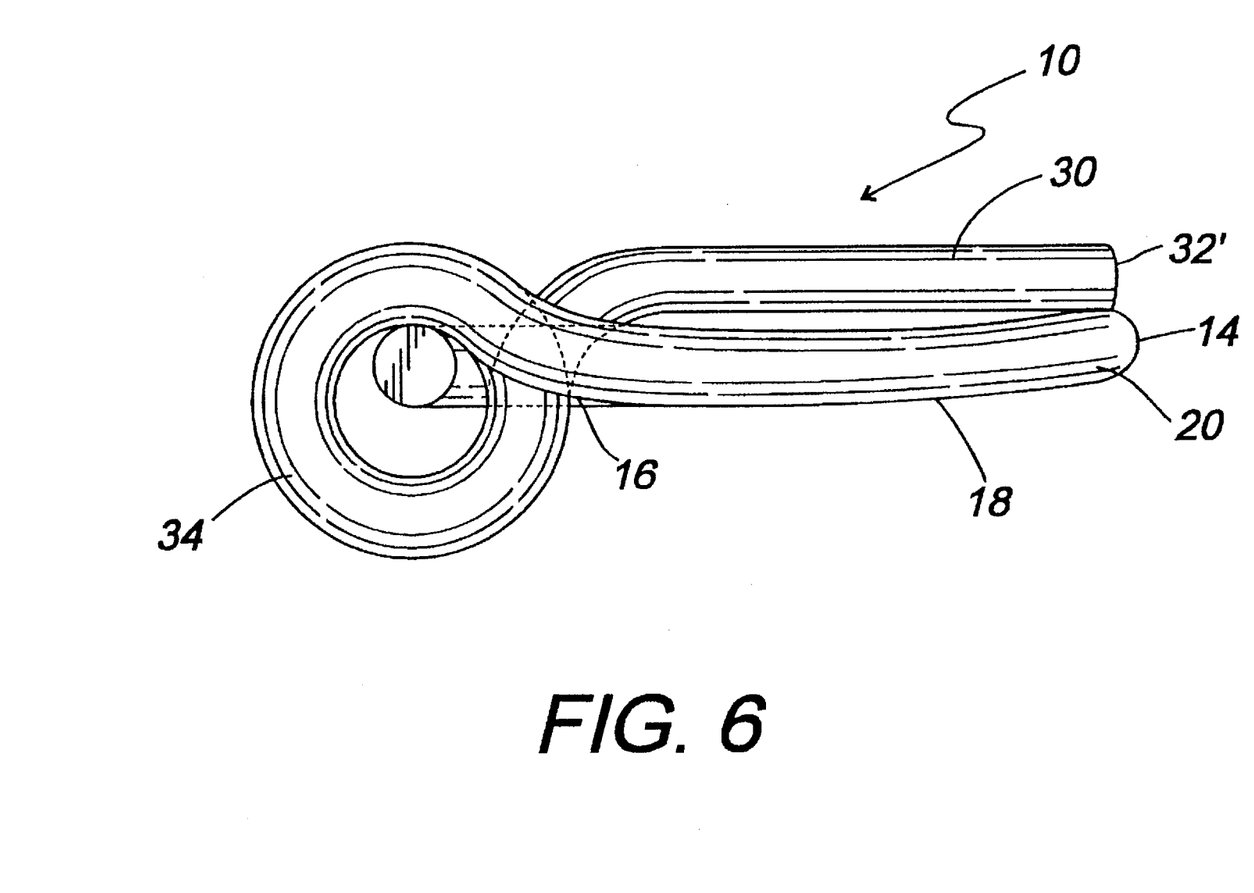
FIG. 6 is a side view of a second embodiment of the surgical clip of the present invention.

A second embodiment of clip 10 is shown in FIGS. 5, 6, with the essential difference from the first embodiment being an extension of clamping arm 30 so that in its "relaxed"

position elongated free end 32' extends over bend section 20 so that, arm 30 rests in a preloaded condition on the upper surface of support member 14, at bend section 20. Accordingly, a preferred length of arm 30 in this embodiment is approximately 7.3 mm with an overall length of clip 10 of approximately 11.4 mm. By extending and preloading arm 30 so that it can assume the position shown in FIG. 6, the cross-sectional area presented by clip 10 is further minimized, rendering it more adaptable for use in small diameter trocars. Preloading arm 30, of course, helps to maintain clip 10 in a narrow profile until it is positioned for application.

As seen in FIG. 6, first arm 16 and second arm 18 of support member 14 are curved upwardly to enhance the clamping force distribution characteristics of clip 10. It will be apparent to those skilled in the art that, as in the first embodiment of FIGS. 1–4, such curvature could be provided alternatively or additionally within clamping arm 30. Where ease of manufacture is a prime objective, each of arms 16, 18, and 30 can be straight.

Figure 7:
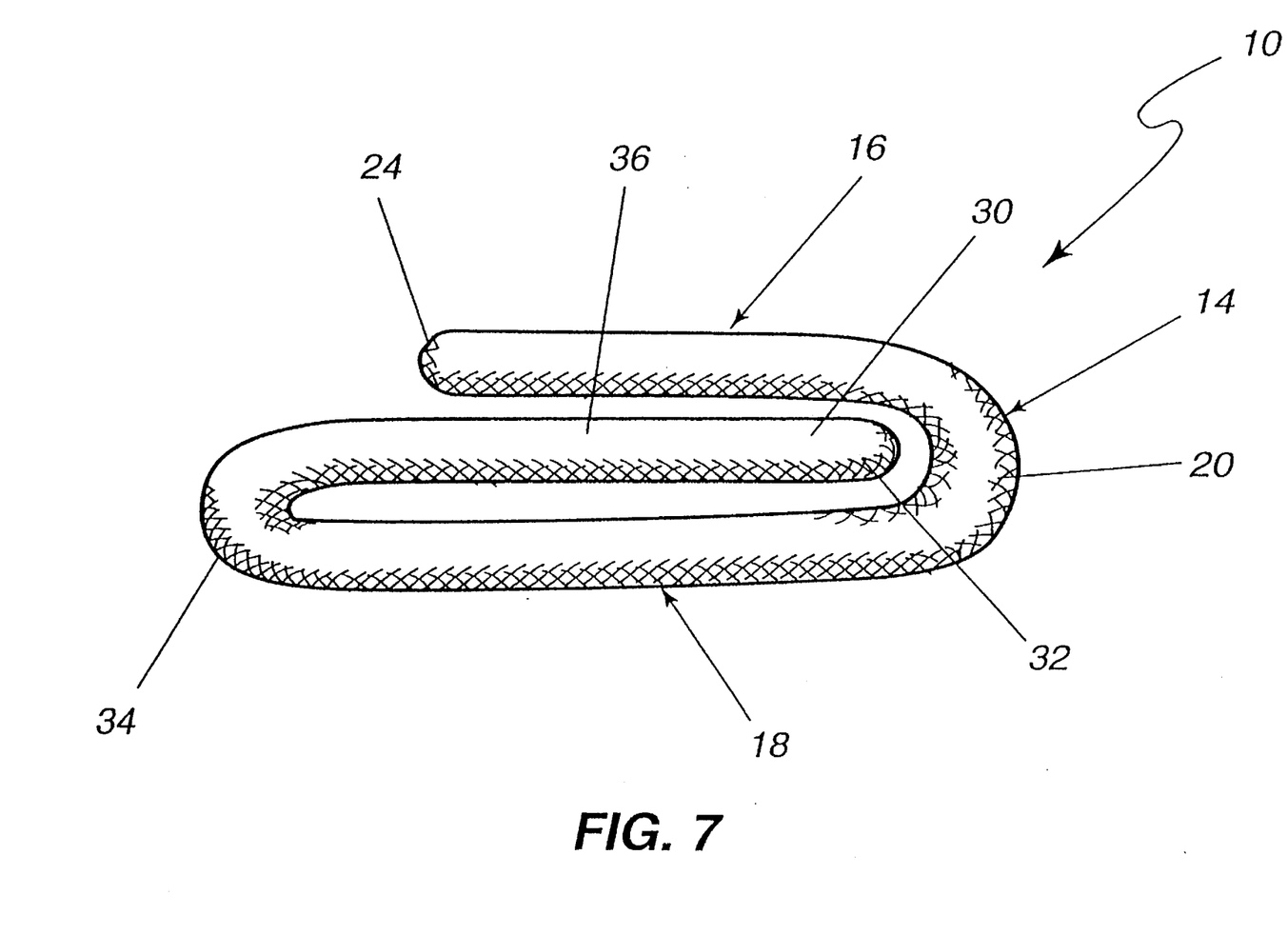
FIG. 7 is a top view of a third embodiment of the surgical clip of the present invention.
Figure 8:
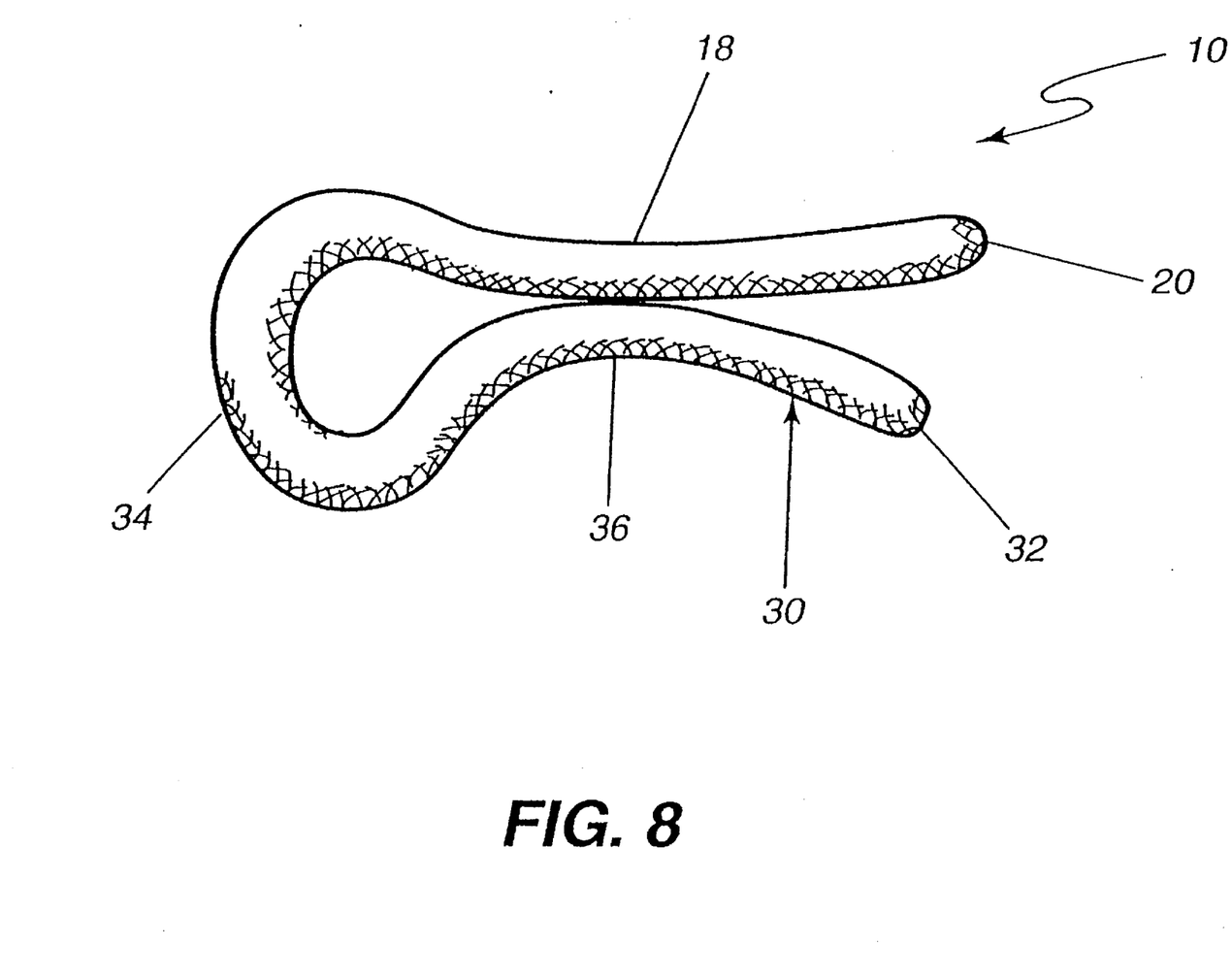
FIG. 8 is a side view of a third embodiment of the surgical clip of the present invention.
Figure 9:
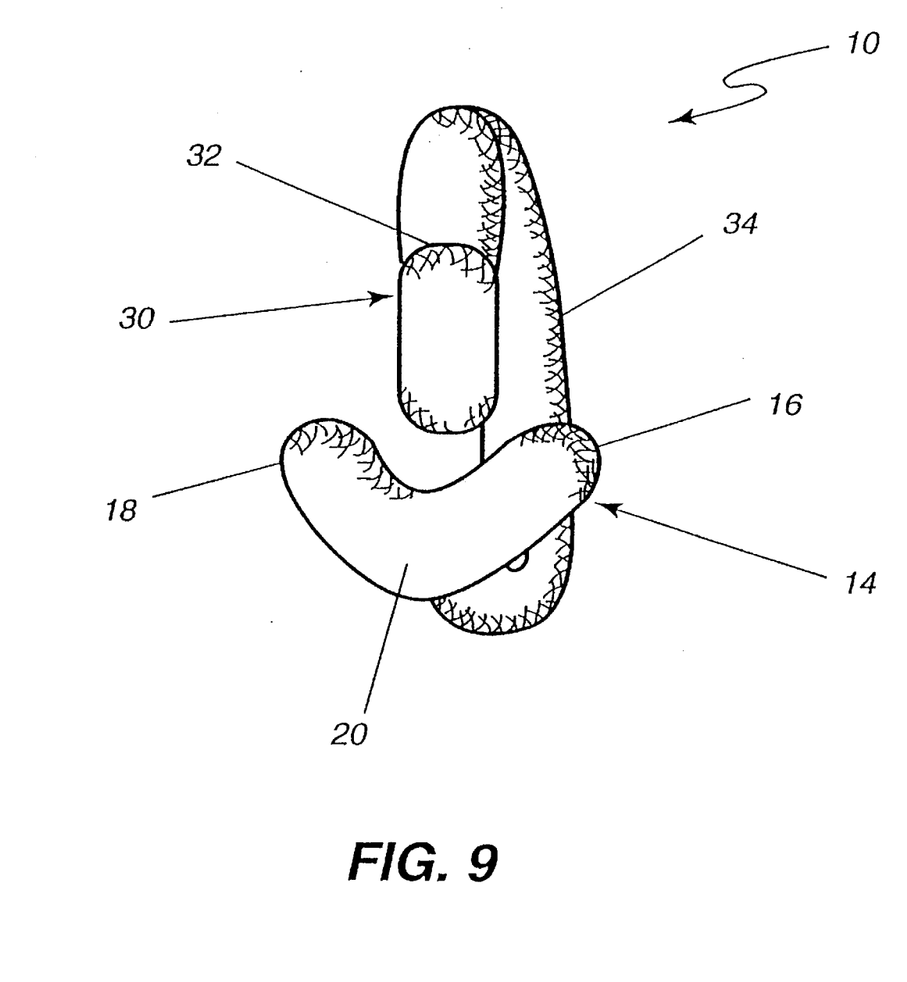
FIG. 9 is an end view of a third embodiment of the surgical clip of the present invention.

A third embodiment of the surgical clip 10 of the present invention is shown in FIGS. 7, 8, and 9. Clamping arm 30 has a curved section 36 extending between distal free end 32 and tension coil 34. Vessel support member 14 is continuously formed of a first arm 16 terminating at proximal free end 24, joined to second arm 18 by one hundred eighty degree (180°) bend section 20. Preferably, bend section 20, as shown in FIG. 9, will also have a generally concave shape so the clamping forces will be distributed more evenly across the surface of the blood vessel (not shown). The shape of curved section 36 of vessel clamping arm 30 is generally convex to provide a more secure holding force to the vessel as well. Although tests have shown that the second embodiment does not perform as well as the first embodiment described above, it does offer the advantage of being simpler to pre-form and perhaps to apply.

Figure 10:
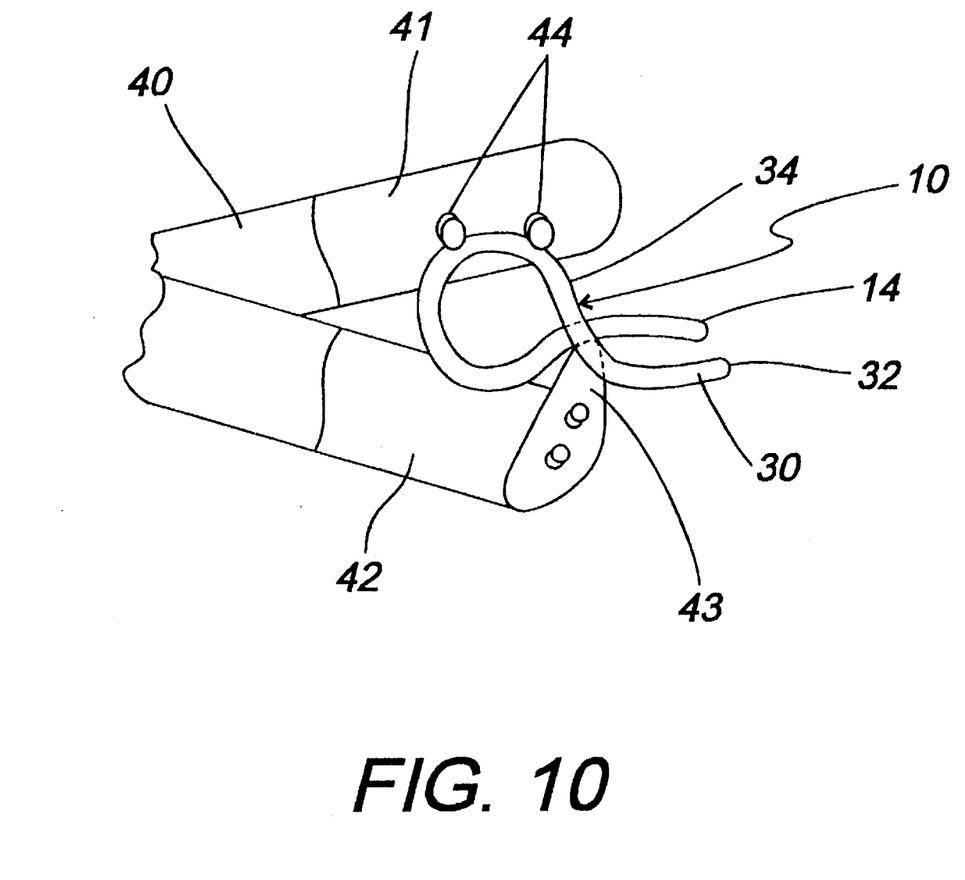
FIG. 10 shows the surgical clip within the jaws of a clip grasper/applier.

FIG. 10 conceptually illustrates the jaw end of a surgical grasper tool 40 which has been modified to function as a clip applier for the surgical clip of the present invention. Slots (not shown) have been machined into the opposing horizontal surfaces of upper jaw 41 and lower jaw 42 to accommodate therein segments of tension coil 34 and loop section 26, thereby orienting clip 10 in the vertical plane. Retaining pins 44 extend perpendicularly from the vertical surfaces of upper jaw 41. A tooth 43 is attached to the vertical surface of lower jaw 42 and extends above jaw 42. When clip 10 is in proper position for application, pins 44 are in contact with tension coil 34 and tooth 43 is in contact with clamping arm 30. Consequently, when jaws 41, 42 are moved toward each other Coy operation of the grasper handle, not shown), pins 44 bear against tension coil 34, and tooth 43 causes clamping arm 30 to move upwardly from its relaxed position. This creates a gap between the free end 32 of arm 30 and the upper surface of support member 14. Clip 10 can then be positioned around the blood vessel (not shown). When jaws 41, 42 are then allowed to move apart, clamping arm 30 is forced downward by tension coil 34 into a clamped position around the vessel. To remove or re-position clip 10, graspers 40 are re-positioned as shown in FIG. 9 and the process is repeated.

Thus, although there have been described particular embodiments of the present invention of a new and useful surgical ligation clip, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What is claimed is:

1. A method of achieving hemostasis of a blood vessel during surgery comprising the steps of:

a. placing a pre-formed surgical ligation clip having a clamping arm, a torsion coil, and a vessel support member through a 5 millimeter or smaller endoscopic trocar port into a surgical field proximate said vessel, said vessel support member comprising a first arm joined to a substantially parallel second arm by a 180 degree bend section, said first arm and said second arm extending in a substantially continuous linear fashion from said torsion coil to said 180 degree bend section, said clamping arm extending in a substantially continuous linear fashion from said torsion coil and horizontally aligned with an opening between said first and second arms of said vessel support member, said clamping arm being in a closed position such that said clamping arm, said vessel support member, and said torsion coil are in substantial longitudinal alignment, and such that said clamping arm and said vessel support member are aligned substantially within the diameter of said torsion coil, to provide a minimum cross-sectional area of said clip while in said closed position during insertion of said clip into the surgical field;

b. bending said clamping arm away from said vessel support member by applying a force directly onto said clamping arm which pushes said clamping arm outwardly with respect to said vessel support member while biasing said torsion coil, thereby placing said clamping arm in an open position;

c. placing said clip around said vessel, whereby said vessel is positioned between said clamping arm and said vessel support member; and d. releasing the force being applied on said clamping arm, thereby placing said vessel under compression between said clamping arm and said vessel support member.

2. The method of claim 1 wherein the diameter of said torsion coil is less than 5 mm.

3. A method of achieving hemostasis of a fluid duct in conjunction with and as a part of an endoscopic surgical procedure comprising the steps of:

a. endoscopically placing a pre-formed surgical ligation clip having a clamping arm, a duct support member and means connecting said arm and said support member and biasing them into clamping juxtaposition into a surgical field proximate said duct by passing said clip through a 5 millimeter or smaller open channel of an endoscopic trocar;

b. compressing said duct to create a reduced diameter prior to placing said clip around said duct;

c. bending said clamping arm away from said duct support member, thereby placing said clamping arm in an open position;

d. placing said clip around the reduced diameter duct whereby said duct is positioned between said clamping arm and said support member; and e. releasing said clamping arm, thereby placing said duct under compression between said clamping arm and said support member.

4. A method of achieving hemostasis of a blood vessel during and as a part of an endoscopic surgical procedure comprising the steps of:

a. placing a pre-formed surgical ligation clip having a clamping arm, a vessel support member and means connecting said clamping arm and said vessel support member and biasing them toward each other through the channel of an endoscopic trocar having a cross-sectional diameter of 5 millimeters or less into a surgical field proximate said vessel;

b. shaping said vessel at a clamping point on said vessel where said clip is to be applied prior to placing said clip around said vessel whereby the shape of said vessel at said clamping point is altered so that said clip, when opened, can fit about said vessel;

c. placing said clip about said vessel at said clamping point, whereby said vessel is positioned between said clamping arm and said vessel support member; and d. compressing said clamping arm into clamping engagement with said vessel support member via said biasing means thereby placing said vessel under compression between said clamping arm and said vessel support member.

* * * * *